US012735371B2

(12) United States Patent
Ashri et al.

(10) Patent No.: US 12,735,371 B2
(45) Date of Patent: Sep. 15, 2026

(54) SYSTEMS AND METHODS FOR LINEAR ALPHA OLEFINS PRODUCTION

(71) Applicant: SABIC GLOBAL TECHNOLOGIES B.V., Bergen op Zoom (NL)

(72) Inventors: Abdulrahman Ashri, Riyadh (SA); Zaid Bin Hazzaa, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 296 days.

(21) Appl. No.: 18/696,288

(22) PCT Filed: Sep. 28, 2022

(86) PCT No.: PCT/EP2022/077038
§ 371 (c)(1),
(2) Date: Mar. 27, 2024

(87) PCT Pub. No.: WO2023/052464
PCT Pub. Date: Apr. 6, 2023

(65) Prior Publication Data

US 2024/0391850 A1 Nov. 28, 2024

(30) Foreign Application Priority Data

Sep. 29, 2021 (EP) .................................... 21199661

(51) Int. Cl.

| | |
|---|---|
| ***C07C 2/36*** | (2006.01) |
| ***B01J 19/00*** | (2006.01) |
| ***B01J 19/24*** | (2006.01) |
| ***C07C 2/30*** | (2006.01) |
| ***C07C 2/34*** | (2006.01) |

(52) U.S. Cl.
CPC ............ *C07C 2/36* (2013.01); *B01J 19/0013* (2013.01); *B01J 19/2435* (2013.01); *C07C 2/30* (2013.01); *C07C 2/34* (2013.01); *B01J 2219/00092* (2013.01); *C07C 2531/14* (2013.01); *C07C 2531/22* (2013.01); *C07C 2531/24* (2013.01)

(58) Field of Classification Search
CPC .... C07C 2/36; C07C 2/30; C07C 2/34; C07C 2531/14; C07C 2531/22; C07C 2531/24; C07C 11/02; C07C 11/107; B01J 19/0013; B01J 19/2435; B01J 2219/00092; B01J 2219/00094; B01J 2219/00162; B01J 2219/00166; B01J 2219/00186; B01J 2219/00247; B01J 19/0026
USPC .......................................................... 585/522
See application file for complete search history.

(56) References Cited

U.S. PATENT DOCUMENTS

| | | | |
|---|---|---|---|
| 4,121,029 | A | 10/1978 | Irvin et al. |
| 2009/0270567 | A1 | 10/2009 | Small et al. |
| 2012/0142989 | A1 | 6/2012 | Jaber et al. |

FOREIGN PATENT DOCUMENTS

| | | | | |
|---|---|---|---|---|
| BR | 112015016333 B1 * | 7/2021 | ............ C08F 210/16 |
| CN | 104056583 A | 9/2014 | |

(Continued)

*Primary Examiner* — Prem C Singh
*Assistant Examiner* — Francis C Campanell
(74) *Attorney, Agent, or Firm* — Womble Bond Dickinson (US) LLP

(57) ABSTRACT

A system and a method for producing oligomers are disclosed. The oligomers are produced in a loop reactor by contacting a mono-olefin with a catalyst. The byproduct produced during the process is collected in one or more settling legs of the loop reactor.

23 Claims, 2 Drawing Sheets

(56) References Cited

FOREIGN PATENT DOCUMENTS

| | | | | | |
|---|---|---|---|---|---|
| CN | 104086349 | B | | 8/2016 | |
| WO | WO-0204119 | A1 | * | 1/2002 | ............. B01J 31/18 |
| WO | WO 2013/013300 | A1 | | 1/2013 | |

* cited by examiner

SYSTEMS AND METHODS FOR LINEAR ALPHA OLEFINS PRODUCTION

CROSS-REFERENCE TO RELATED APPLICATIONS

The present application is a 371 U.S. national stage application of International Application No. PCT/EP2022/077038, filed Sep. 28, 2022, which claims priority from European Application No. 21199661.6, filed Sep. 29, 2021, all of which are incorporated herein by reference in their entirety.

FIELD OF INVENTION

The present invention generally relates to systems and methods for producing oligomers. More specifically, the present invention relates to systems and methods for producing linear alpha olefins in loop reactors.

BACKGROUND OF THE INVENTION

Linear alpha olefins are used in a wide range of applications including packaging, industrial oils, waxes, engines, and other specialty chemicals. Linear alpha olefins can also be used as starting materials for development of new chemicals, such as surfactants.

Currently, linear alpha olefins are produced by Fischer-Tropsch synthesis or oligomerization of ethylene. For Fischer-Tropsch synthesis, the reaction rate is generally low, resulting in high production costs. Furthermore, the reactor design for Fisher-Tropsch synthesis is usually complex and the product purification process for Fischer-Tropsch synthesis is extensive, thereby requiring high capital expenditure. For the process of oligomerization of ethylene, reactor fouling and dead spots are the main issues that limit the efficiency and production cost for linear alpha olefins.

Overall, while systems and methods for producing linear alpha olefins exist, the need for improvements in this field persists in light of at least the aforementioned drawbacks for the conventional systems and methods.

BRIEF SUMMARY OF THE INVENTION

A solution to at least some of the above mentioned problems associated with systems and methods for producing linear alpha olefins is disclosed. The solution resides in a system and a method for producing oligomers that uses a loop reactor. This can be beneficial for at least improving the homogeneity of the reaction mixture for oligomerizing olefins. Additionally, all the reaction materials in the loop reactor can be in liquid phase, thus improving the temperature distribution and temperature control in the reactor. Furthermore, the loop reactor is capable of reducing the formation of dead spots (i.e., accumulated materials) and fouling, resulting in improved production efficiency. Moreover, the loop reactor can include settling legs configured to settle and collect the byproduct polymers from the reaction materials during the reaction process, thereby reducing the burden for downstream purification. The settling legs can be removable for cleaning purposes without disturbing or stopping the oligomerization reaction in the loop reactor, thereby further improving the production efficiency. Therefore, the systems and methods of the present invention provide a technical solution to the problem associated with the conventional systems and methods for producing linear alpha olefins.

Embodiments of the invention include a method for producing oligomers. The method comprises contacting, in a loop reactor, a mono-olefin with a catalyst under reaction conditions sufficient to oligomerize the mono-olefin to produce a product stream comprising (1) one or more oligomers and (2) a byproduct comprising one or more waxes/polymers. The loop reactor comprises a loop-shaped tubing container configured to receive the mono-olefin and the catalyst therein and one or more settling legs configured to settle and/or collect the byproduct.

Embodiments of the invention include a method for producing one or more linear alpha olefins. The method comprises contacting, in a loop reactor, a mono-olefin with a catalyst under reaction conditions sufficient to oligomerize the mono-olefin to produce a product stream comprising (1) one or more oligomers and (2) a byproduct comprising one or more polymers. The loop reactor comprises (a) a loop-shaped tubing container configured to receive the mono-olefin and the catalyst therein and (b) one or more settling legs in fluid communication with the loop-shaped tubing container. The method comprises collecting at least some of the byproduct from the product stream in the one or more settling legs.

Embodiments of the invention include a method for producing 1-hexene and/or 1-octene. The method comprises contacting, in a loop reactor, ethylene with a catalyst under reaction conditions sufficient to oligomerize the ethylene to produce a product stream comprising (1) 1-hexene and/or 1-octene and (2) a byproduct comprising one or more ethylene polymers. The loop reactor comprises (a) a loop-shaped tubing container configured to receive ethylene and the catalyst therein and (b) one or more settling legs in fluid communication with the loop-shaped tubing container. The method comprises collecting at least some of the byproduct from the product stream in the one or more settling legs. In any embodiment noted herein, the loop reactor can comprise one or more nozzles and/or one or more filters configured to limit fouling therein. In any embodiment noted herein, the reaction conditions can include a reaction temperature in a range of 20 to 80° C. and/or a reaction pressure of 15 to 35 bar.

The present disclosure includes, without limitation, the following example embodiments:

Embodiment 1: A method for producing oligomers, the method comprising:

- contacting, in a loop reactor, a mono-olefin with a catalyst under reaction conditions sufficient to oligomerize the mono-olefin to produce a product stream comprising (1) one or more oligomers and (2) a byproduct comprising one or more waxes and/or polymers,
- wherein the loop reactor comprises a loop-shaped tubing container configured to receive the mono-olefin and the catalyst therein and one or more settling legs configured to settle and/or collect the byproduct; and
- receiving untreated byproduct into the one or more settling legs directly from the loop-shaped tubing container.

Embodiment 2: The method of Embodiment 1, wherein a valve positioned between the loop-shaped tubing container and the one or more settling legs prevents backflow into the loop-shaped tubing container.

Embodiment 3: The method of Embodiment 1 or 2, wherein the untreated byproduct does not contact a treatment fluid before entering the one or more settling legs.

Embodiment 4: The method of any one of Embodiments 1-3, further comprising a pump configured to pump the mono-olefin and catalyst through the loop-shaped tubing container, wherein the distance between the one or more settling legs and an upstream side of the pump is no more than about 5 percent of the total linear length of the loop-shaped tubing container.

Embodiment 5: The method of any one of Embodiments 1-4, wherein the distance between the one or more settling legs and an upstream side of the pump is no more than about 5 meters of total linear length of the loop-shaped tubing container.

Embodiment 6: The method of any one of Embodiments 1-5, wherein the loop reactor comprises a shell-and-tube configuration with a tube comprising the loop-shaped tubing container configured to receive the mono-olefin and the catalyst therein and a shell configured to receive heating and/or cooling medium.

Embodiment 7: The method of any one of Embodiments 1-6, wherein the loop reactor has a substantially constant temperature profile.

Embodiment 8: The method of any one of Embodiments 1-7, wherein the reaction conditions include a reaction temperature in a range of 20 to 80° C.

Embodiment 9: The method of any one of Embodiments 1-8, wherein the reaction conditions include a reaction temperature in a range of 65 to 75° C.

Embodiment 10: The method of any one of Embodiments 1-9, wherein the one or more oligomers include one or more linear alpha olefins.

Embodiment 11: The method of any one of Embodiments 1-10, wherein the one or more oligomers include 1-hexene and/or 1-octene.

Embodiment 12: The method of any one of Embodiments 1-11, wherein the reaction conditions include a reaction pressure of 15 to 35 bar.

Embodiment 13: The method of any one of Embodiments 1-12, wherein the product stream comprises greater than 0 wt % but no more than 60 wt % 1-hexene and/or 1-octene.

Embodiment 14: The method of any one of Embodiments 1-13, wherein the one or more settling legs are adapted to be removable for cleaning without interfering with operation of the loop reactor.

Embodiment 15: The method of any one of Embodiments 1-14, wherein the catalyst includes $Cr(acac)_3$, PNPNH, triethylaluminum, or combinations thereof.

Embodiment 16: The method of any one of Embodiments 1-15, wherein the mono-olefin is fed into the loop reactor with a solvent and/or diluent comprising xylene, toluene, heptane, modified methylaluminoxane (MMAO), n-hexane, cyclohexane, or combinations thereof.

Embodiment 17: The method of any one of Embodiments 1-16, wherein the catalyst has a concentration in the loop reactor of no more than 10 wt %.

Embodiment 18: The method of any one of Embodiments 1-17, wherein the loop reactor is configured to reduce dead spot therein compared to non-loop reactors.

Embodiment 19: The method of any one of Embodiments 1-18, wherein the loop reactor is operated with a residence time of less than 1000 minutes.

Embodiment 20: A system for producing oligomers, the system comprising:

- a supply of mono-olefin and a supply of catalyst;
- a loop reactor comprising a loop-shaped tubing container in fluid communication with the supply of mono-olefin and the supply of catalyst, the loop reactor adapted to oligomerize the mono-olefin to produce a product comprising one or more oligomers and a byproduct comprising one or more waxes and/or polymers; and
- one or more settling legs in fluid communication with the loop-shaped tubing container and positioned to receive an untreated byproduct stream directly from the loop-shaped tubing container.

Embodiment 21: The system of Embodiment 20, further comprising a valve positioned between the loop-shaped tubing container and the one or more settling legs configured to prevent backflow into the loop-shaped tubing container.

Embodiment 22: The system of Embodiment 20 or 21, further comprising a pump configured to pump the mono-olefin and catalyst through the loop-shaped tubing container, wherein the distance between the one or more settling legs and an upstream side of the pump is no more than about 5 percent of the total linear length of the loop-shaped tubing container.

Embodiment 23: The system of any one of Embodiments 20-22, wherein the distance between the one or more settling legs and an upstream side of the pump is no more than about 5 meters of total linear length of the loop-shaped tubing container.

Embodiment 24: The system of any one of Embodiments 20-23, wherein the loop reactor comprises a shell-and-tube configuration with a tube comprising the loop-shaped tubing container configured to receive the mono-olefin and the catalyst therein and a shell configured to receive heating and/or cooling medium.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise The following includes definitions of various terms and phrases used throughout this specification.

The terms “about” or “approximately” are defined as being close to as understood by one of ordinary skill in the art. In one non-limiting embodiment the terms are defined to be within 10%, preferably, within 5%, more preferably, within 1%, and most preferably, within 0.5%.

The terms “wt %”, “vol %” or “mol %” refer to a weight, volume, or molar percentage of a component, respectively, based on the total weight, the total volume, or the total moles of material that includes the component. In a non-limiting example, 10 moles of component in 100 moles of the material is 10 mol % of component.

The term “substantially” and its variations are defined to include ranges within 10%, within 5%, within 1%, or within 0.5%.

The terms “inhibiting” or “reducing” or “preventing” or “avoiding” or any variation of these terms, when used in the claims and/or the specification, include any measurable decrease or complete inhibition to achieve a desired result.

The term “effective,” as that term is used in the specification and/or claims, means adequate to accomplish a desired, expected, or intended result.

The term “loop reactor,” as that term is used in the specification and/or claims means continuous tube or pipe shaped reactor, in which a reaction mixture is circulated in a loop.

The term “reaction materials,” as that term is used in the specification and/or claims means the materials that are contained in a reactor. In embodiments of the invention, the reaction materials include all the materials contained in the tube of the loop reactor. In embodiments of the invention, the reaction materials include one or more mono-olefins, one or more oligomers, one or more solvents and/or diluents, and one or more byproducts.

The use of the words “a” or “an” when used in conjunction with the term “comprising,” “including,” “containing,” or “having” in the claims or the specification may mean “one,” but it is also consistent with the meaning of “one or more,” “at least one,” and “one or more than one.”

The words “comprising” (and any form of comprising, such as “comprise” and “comprises”), “having” (and any form of having, such as “have” and “has”), “including” (and any form of including, such as “includes” and “include”) or “containing” (and any form of containing, such as “contains” and “contain”) are inclusive or open-ended and do not exclude additional, unrecited elements or method steps.

The process of the present invention can “comprise,” “consist essentially of,” or “consist of” particular ingredients, components, compositions, etc., disclosed throughout the specification.

The term “primarily,” as that term is used in the specification and/or claims, means greater than any of 50 wt %, 50 mol %, and 50 vol %. For example, “primarily” may include 50.1 wt % to 100 wt % and all values and ranges there between, 50.1 mol % to 100 mol % and all values and ranges there between, or 50.1 vol % to 100 vol % and all values and ranges there between.

Other objects, features and advantages of the present invention will become apparent from the following figures and detailed description. It should be understood, however, that the figures and detailed description, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, linear alpha olefins are produced via Fischer-Tropsch synthesis or oligomerization of ethylene. Fischer-Tropsch synthesis often suffers from issues including low reaction rate and complex reactor design. Oligomerization of ethylene for producing linear alpha olefins, on the other hand, often has to deal with the drawbacks of reactor fouling and dead spots in the reactors. The present invention provides a solution to at least some of these problems. The solution is premised on a method of producing oligomers in a loop reactor that facilitates improved homogeneity of reaction materials in the reactor, resulting in improved temperature distribution and temperature control in the reactor. Therefore, the loop reactor used in the disclosed method is configured to limit the formation of dead spots (i.e., accumulated materials) and fouling in the reactor, thereby improving production efficiency for linear alpha olefins. These and other non-limiting aspects of the present invention are discussed in further detail in the following sections.

A. System for Producing Oligomers

Figure 1:
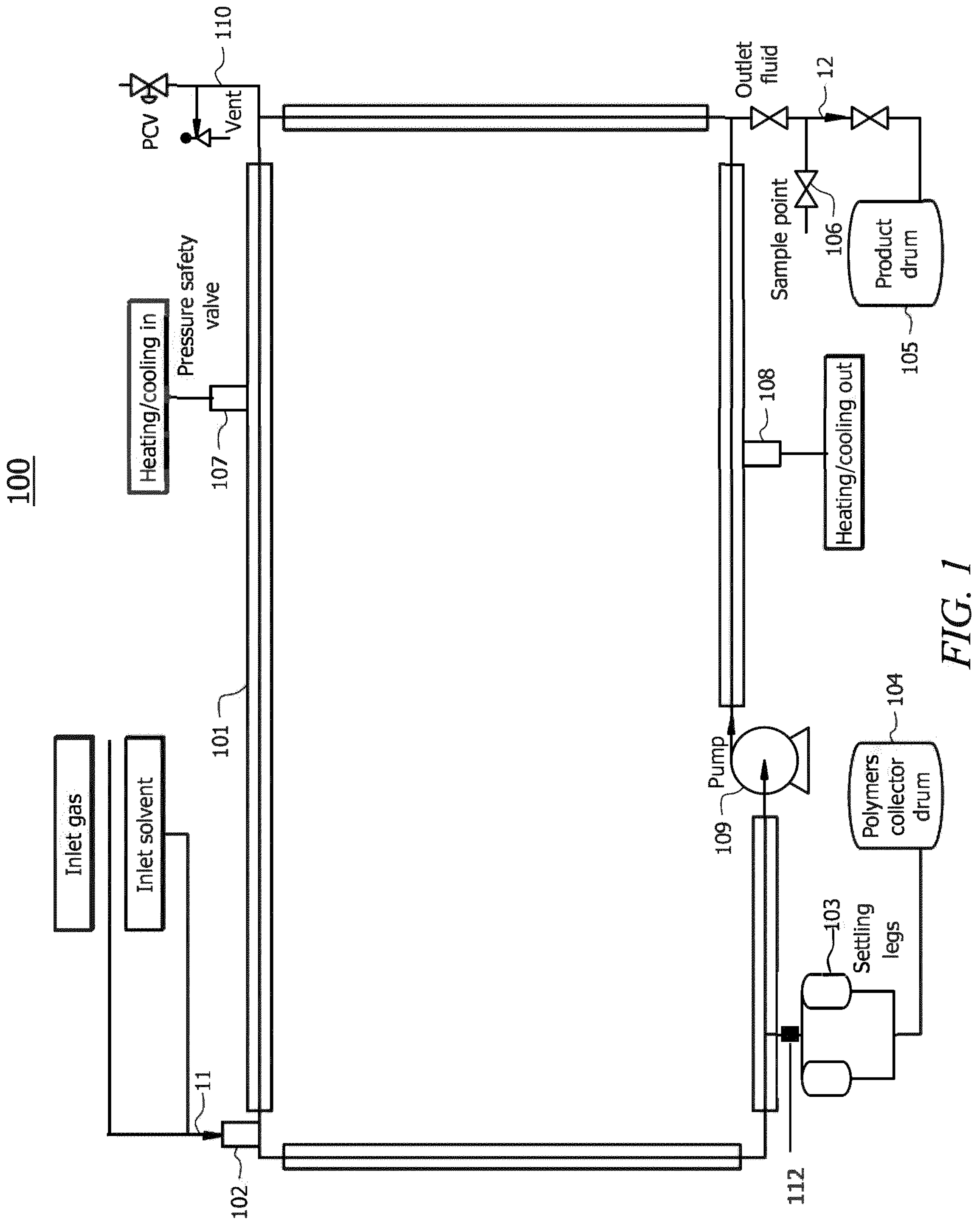
FIG. 1 shows a schematic diagram for a system of producing oligomers, according to embodiments of the invention.

In embodiments of the invention, the system for producing oligomers, including linear alpha olefins, includes a loop reactor adapted to reduce dead spot and limit fouling compared to non-loop reactors. With reference to FIG. 1, a schematic diagram is shown for reactor 100 for producing oligomers.

According to embodiments of the invention, reactor 100 is a loop reactor configured to produce oligomers from one or more olefins. In embodiments of the invention, the oligomers can include one or more linear alpha olefins. The one or more olefins can include ethylene. Exemplary linear alpha olefins can include 1-hexene and/or 1-octene.

According to embodiments of the invention, reactor 100 can include reactor body 101 configured to contain reaction materials therein. In embodiments of the invention, reactor body 101 includes a loop-shaped tubing container. Reactor body 101 can have a shell-and-tube configuration with the reaction materials (process fluid) contained in the tube (i.e., the tubing container) and heating and/or cooling medium contained in the shell of reactor body 101. In embodiments of the invention, reactor body 101 can be made of stainless steel, carbon steel, or combinations thereof. In embodiments of the invention, reactor body 101 has a total length to inner diameter (diameter for the tube) ratio in a range of 20 to 2000. Reactor body 101 can have a shell-to-tube diameter ratio in a range of 2 to 20 and all ranges and values there between including ranges of 2 to 4, 4 to 6, 6 to 8, 8 to 10, 10 to 12, 12 to 14, 14 to 16, 16 to 18, and 18 to 20.

According to embodiments of the invention, reactor 100 includes feed inlet 102 configured to receive feed stream 11 into reactor body 101. In embodiments of the invention, feed stream 11 includes a feed gas and/or a catalyst for oligomerization. Feed stream 11 can further include a solvent and/or a diluent. Exemplary feed gas can include ethylene, hydrogen, nitrogen, isopentane, and combinations thereof. The catalyst can include $Cr(acac)_3$, PNPNH, triethylaluminum (TEAL), or combinations thereof. The solvent and/or diluent can include xylene, toluene, heptane, modified methylaluminoxane (MMAO), n-hexane, cyclohexane, or combinations thereof.

According to embodiments of the invention, reactor 100 comprises at least one settling leg 103 in fluid communication with the tube of reactor body 101 such that at least some byproduct produced in the tube of reactor body 101 is collected in the settling leg 103. In embodiments of the invention, an outlet of settling leg 103 is in fluid communication with collector drum 104 such that byproduct collected in settling leg 103 is further flowed into collector drum 104. In embodiments of the invention, reactor 100 comprises one or more settling legs 103 and one or more settling legs 103 can share one collector drum 104, or alternatively each settling leg 103 is connected to a separate collector drum 104.

In embodiments of the invention, one or more settling legs 103 are adapted to be removable for cleaning without interfering the operation of reactor 100. As shown in FIG. 1, in certain embodiments, a plurality of settling legs 103 are arranged in parallel with each settling leg in fluid communication with the tube of reactor body 101. In this manner, one of the plurality of settling legs 103 can be removed/detached from the system for cleaning without disrupting operation of the reactor 100.

As shown in FIG. 1, it is advantageous for the settling legs 103 to have direct fluid communication with the tube of the reactor body 101 with no intervening unit operation structure or treatment therebetween. In this manner, byproduct from the reactor body 101 can be collected in the settling legs 103 with no intervening treatment that could lead to backflow into the reactor body 101. For example, if the byproduct leaving the reactor body 101 is contacted with a solvent prior to entering the settling leg, there is a possibility of contamination of the reaction materials within the reactor 101. Such contamination could lead to additional undesirable polymeric byproduct formation and/or crystallization. Accordingly, as used herein, reference to "untreated byproduct" refers to byproduct entering the settling legs 103 directly from the reactor body 101 without contacting any treatment fluid intended to change the characteristics of the byproduct and/or intended to backflow into the reactor body 101.

A valve 112 is positioned between the settling legs 103 and the reactor body 101. The valve 112 allows untreated byproduct to flow from the reactor body 101 into the settling legs 103, and is typically configured to prevent backflow from the settling legs into the reactor. In this manner, contamination of the reactor with polymeric byproduct from the settling legs can be prevented or reduced. Accordingly, the valve 112 structure can perform multiple functions, or consist of an assembly of components that perform different functions, including opening and closing a fluid connection between the reactor body 101 and the settling legs 103, and preventing backflow from the settling legs into the reactor body. Example valve and backflow structures that can be used as part of valve 112 include double check valves, pressure vacuum breakers, swing check valves, double disc valves, lift check valves, and ball check valves. The valve 112 can be either mechanically or electronically actuated or otherwise controlled.

According to embodiments of the invention, a product outlet of the tube of reactor body 101 is in fluid communication with product drum 105 such that product stream 12 comprising the oligomers flows from the tube into product drum 105. In embodiments of the invention, reactor 100 comprises sample port 106 in fluid communication with the product outlet of reactor body 101 and product drum 105 such that at least a sample of the product from the tube of reactor body 101 is flowed out from sample port 106.

According to embodiments of the invention, reactor 100 comprises heating medium inlet 107 configured to receive heating medium into the shell of reactor body 101. Exemplary heating medium can include water. In embodiments of the invention, reactor 100 can comprise heating medium outlet 108 configured to release heating medium from the shell of reactor body 101. In embodiments of the invention, reactor 100 can include pump 109 configured to move materials in the tube of reactor body 101 inside the tube. Pump 109 can include axile pump, centrifugal pump, or positive displacement pump. According to embodiments of the invention, reactor 100 comprises vent 110 in fluid communication with the tube of reactor body 101 such that unreacted feed gases, nitrogen, oxygen or any combination thereof is vented from reactor 100.

According to embodiments of the invention, settling legs 103 are located before pump 109 such that the byproduct is removed from reactor body 101, thereby mitigating and/or preventing fouling of pump 109 by the byproduct. Placement of the settling legs 103 upstream and proximal to the pump 109 is advantageous to reduce polymer byproduct fouling of the pump and also serves to enhance product recovery downstream of the pump. In certain embodiments, the fluid connection between the reactor body 101 and the settling legs 103 is placed within about 5 meters (e.g., within about 4 meters or within about 3 meters or within about 2 meters) of the upstream side of the pump 109, measured in terms of the linear length of reactor body 101 between the fluid connection with the settling legs and the upstream side (i.e., inlet side) of the pump. In another embodiment, the distance between the fluid connection with the settling legs 103 and the upstream side of the pump can be quantified in terms of the percentage of the total linear length of the reactor body 101 that is located between the settling legs and the pump. For example, in certain embodiments, the percentage of the total linear length of the reactor between the settling legs and the pump is no more than about 5 percent, or no more than about 4 percent, or no more than about 3 percent, or no more than about 2 percent. In other words, if the total linear length of reactor body 101 is 200 meters, the distance between the settling legs and the pump is no more than about 10 meters.

In embodiments of the invention, reactor 100 comprises one or more nozzles and/or one or more filters in settling legs 103 configured to limit fouling in pump 109 by the byproduct. For example, a mesh screen can be placed upstream of the settling legs 103 and either upstream or downstream of the valve 112 in order to avoid solid particulates from entering the settling legs.

B. Method of Producing Oligomers

Figure 2:
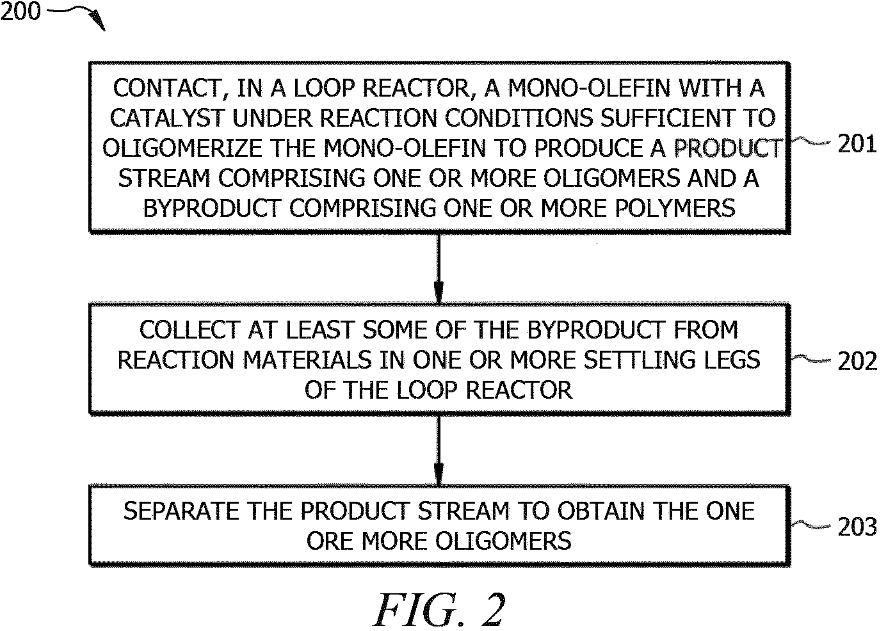
FIG. 2 shows a schematic flowchart for producing oligomers, according to embodiments of the invention.

Methods of producing oligomers, including linear alpha olefins, have been discovered. As shown in FIG. 2, embodiments of the invention include method 200 for producing oligomers with improved production efficiency and reduced fouling and dead spots in the reactors, compared to conventional methods. Method 200 may be implemented by reactor 100, as shown in FIG. 1 and described above.

According to embodiments of the invention, as shown in block 201, method 200 includes contacting, in reactor 100, a mono-olefin with a catalyst under reaction conditions sufficient to oligomerize the mono-olefin to produce product stream 12 comprising one or more oligomers and a byproduct comprising one or more polymers. In embodiments of the invention, the oligomers comprise one or more linear alpha olefins. Exemplary linear alpha olefins include 1-hexene, 1-octene, 1-butene, 1-decene, and combinations thereof. In embodiments of the invention, the mono-olefin includes ethylene. Exemplary catalyst comprises $Cr(acac)_3$, PNPNH, TEAL, and combinations thereof.

In embodiments of the invention, at block 201, the mono-olefin and the catalyst are mixed with a solvent and/or a diluent. Exemplary solvents and/or diluents include xylene, heptane, MMAO, toluene, n-hexane, cyclohexane, and combinations thereof. In embodiments of the invention, prior to the contacting step at block 201, feed stream 11 is flowed into the tube of reactor body 101. Feed stream 11 can include 1 to 100 wt % mono-olefins, 0 to 50 wt % catalyst, and 0 to 100 wt % solvent. The byproduct, in embodiments of the invention, comprises polyethylene.

In embodiments of the invention, the product is 1-hexene, and the reaction conditions at block 201 include a reaction temperature of 20 to 80° C. and all ranges and values there between including ranges of 20 to 25° C., 25 to 30° C., 30 to 35° C., 35 to 40° C., 40 to 45° C., 45 to 50° C., 50 to 55° C., 55 to 60° C., 60 to 65° C., 65 to 70° C., 70 to 75° C., and 75 to 80° C. In embodiments of the invention, the product is 1-hexene and the reaction conditions at block 201 include a reaction pressure of 15 to 35 bar and all ranges and values there between including ranges of 15 to 17 bar, 17 to 19 bar, 19 to 21 bar, 21 to 23 bar, 23 to 25 bar, 25 to 27 bar, 27 to 29 bar, 29 to 31 bar, 31 to 33 bar, and 33 to 35 bar. In embodiments of the invention, the product is 1-hexene and the reaction conditions at block 201 include a residence time of 10 to 1000 minutes. In embodiments of the invention, the product is 1-octene, and the reaction conditions at block 201 include a reaction temperature of 20 to 80° C. and all ranges and values there between including ranges of 20 to 25° C., 25 to 30° C., 30 to 35° C., 35 to 40° C., 40 to 45° C., 45 to 50° C., 50 to 55° C., 55 to 60° C., 60 to 65° C., 65 to 70° C., 70 to 75° C., and 75 to 80° C. In certain embodiments, the reactor maintains a substantially constant temperature profile, such as a substantially constant temperature profile that maintains the temperature within one of the above ranges. In embodiments of the invention, the product is 1-octene and the reaction conditions at block 201 include a reaction pressure of 15 to 35 bar and all ranges and values there between including ranges of 15 to 17 bar, 17 to 19 bar, 19 to 21 bar, 21 to 23 bar, 23 to 25 bar, 25 to 27 bar, 27 to 29 bar, 29 to 31 bar, 31 to 33 bar, and 33 to 35 bar. In embodiments of the invention, the product is 1-octene and the reaction conditions at block 201 include a residence time of 10 to 1000 minutes. In embodiments of the invention, reaction kinetics in reactor 100 substantially follows reaction kinetics of a continuous stirred-tank reactor (CSTR). According to embodiments of the invention, contacting step at block 201 is conducted in liquid phase. Reactor 100 can have a substantially constant temperature profile (i.e., substantially uniform temperature throughout the loop reactor) therein. In embodiments of the invention, product stream 12 includes greater than 0 wt % but no more than 60 wt % of the product, and 0 to 50 wt % of the byproduct. In embodiments of the invention, product stream 12 is flowed into product drum 105. In embodiments of the invention, product stream 12 includes greater than 0 wt % but no more than 60 wt % 1-hexene and all ranges and values there between including ranges of 0.00001 wt % to 5 wt %, 5 to 10 wt %, 10 to 15 wt %, 15 to 20 wt %, 20 to 25 wt %, 25 to 30 wt %, 30 to 35 wt %, 35 to 40 wt %, 40 to 45 wt %, 45 to 50 wt %, 50 to 55 wt %, and 55 to 60 wt %. In embodiments of the invention, product stream 12 includes greater than 0 wt % but no more than 60 wt % 1-octene and all ranges and values there between including ranges of 0.00001 wt % to 5 wt %, 5 to 10 wt %, 10 to 15 wt %, 15 to 20 wt %, 20 to 25 wt %, 25 to 30 wt %, 30 to 35 wt %, 35 to 40 wt %, 40 to 45 wt %, 45 to 50 wt %, 50 to 55 wt %, and 55 to 60 wt %.

According to embodiments of the invention, as shown in block 202, method 200 includes collecting at least some of the byproduct from reaction materials in one or more settling legs 103. The byproduct in the settling legs 103 may be further flowed from settling legs 103 to collector drum 104. In embodiments of the invention, the conversion rate of the ethylene in method 200 is in a range of 0 to 100%. According to embodiments of the invention, as shown in block 203, method 200 includes separating product stream 12 to obtain the one or more oligomers. In embodiments of the invention, the separating at block 203 is conducted using batch distillation, column distillation, or combinations thereof. According to embodiments of the invention, for method 200, the selectivity for producing linear alpha olefins is between 0 to 100.

According to embodiments of the invention, when switching target product for method 200, the tube of reactor body 101 is cleaned via hot boiling or hot flushing using a cleaning medium. In embodiments of the invention, the cleaning medium can include heptane, xylene, isopentane, or combinations thereof. The hot boiling or hot flushing can be conducted at a temperature in a range of 20 to 200° C.

Although embodiments of the present invention have been described with reference to blocks of FIG. 2 should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for producing oligomers, the method comprising:

contacting, in a loop reactor, a mono-olefin with a catalyst under reaction conditions sufficient to oligomerize the mono-olefin to produce a product stream comprising (1) one or more oligomers and (2) a byproduct comprising one or more waxes and/or polymers, wherein the loop reactor comprises a loop-shaped tubing container configured to receive the mono-olefin and the catalyst therein and one or more settling legs configured to settle and/or collect the byproduct;

withdrawing a product stream comprising one or more oligomers from the loop reactor through a product outlet; and receiving untreated byproduct into the one or more settling legs directly from the loop-shaped tubing container.

2. The method of claim 1, wherein a valve positioned between the loop-shaped tubing container and the one or more settling legs prevents backflow into the loop-shaped tubing container.

3. The method of claim 1, wherein the untreated byproduct does not contact a treatment fluid before entering the one or more settling legs.

4. The method of claim 1, further comprising a pump configured to pump the mono-olefin and catalyst through the loop-shaped tubing container, wherein the distance between the one or more settling legs and an upstream side of the pump is no more than about 5 percent of the total linear length of the loop-shaped tubing container.

5. The method of claim 4, wherein the distance between the one or more settling legs and an upstream side of the pump is no more than about 5 meters of total linear length of the loop-shaped tubing container.

6. The method of claim 1, wherein the loop reactor comprises a shell-and-tube configuration with a tube comprising the loop-shaped tubing container configured to receive the mono-olefin and the catalyst therein and a shell configured to receive heating and/or cooling medium.

7. The method of claim 1, wherein the loop reactor has a substantially constant temperature profile.

8. The method of claim 7, wherein the reaction conditions include a reaction temperature in a range of 20 to 80° C.

9. The method of claim 8, wherein the reaction conditions include a reaction temperature in a range of 65 to 75° C.

10. The method of claim 1, wherein the one or more oligomers include one or more linear alpha olefins.

11. The method of claim 10, wherein the one or more oligomers include 1-hexene and/or 1-octene.

12. The method of claim 1, wherein the reaction conditions include a reaction pressure of 15 to 35 bar.

13. The method of claim 1, wherein the product stream comprises greater than 0 wt % but no more than 60 wt % 1-hexene and/or 1-octene.

14. The method of claim 1, wherein the one or more settling legs are adapted to be removable for cleaning without interfering with operation of the loop reactor.

15. The method of claim 1, wherein the catalyst includes Chromium (III) acetylacetonate, a ligand with a PNPNH backbone, triethylaluminum, or combinations thereof.

16. The method of claim 1, wherein the mono-olefin is fed into the loop reactor with a solvent and/or diluent comprising xylene, toluene, heptane, modified methylaluminoxane (MMAO), n-hexane, cyclohexane, or combinations thereof.

17. The method of claim 1, wherein the catalyst has a concentration in the loop reactor of no more than 10 wt %.

18. The method of claim 1, wherein the loop reactor is operated with a residence time of less than 1000 minutes.

19. A system for producing oligomers, the system comprising:

a supply of mono-olefin and a supply of catalyst;

a loop reactor comprising a loop-shaped tubing container in fluid communication with the supply of mono-olefin and the supply of catalyst, the loop reactor adapted to oligomerize the mono-olefin to produce a product comprising one or more oligomers and a byproduct comprising one or more waxes and/or polymers;

a product outlet in fluid communication with the loop reactor for receiving a product stream comprising one or more oligomers; and one or more settling legs in fluid communication with the loop-shaped tubing container and positioned to receive an untreated byproduct stream directly from the loop-shaped tubing container.

20. The system of claim 19, further comprising a valve positioned between the loop-shaped tubing container and the one or more settling legs configured to prevent backflow into the loop-shaped tubing container.

21. The system of claim 19, further comprising a pump configured to pump the mono-olefin and catalyst through the loop-shaped tubing container, wherein the distance between the one or more settling legs and an upstream side of the pump is no more than about 5 percent of the total linear length of the loop-shaped tubing container.

22. The system of claim 21, wherein the distance between the one or more settling legs and an upstream side of the pump is no more than about 5 meters of total linear length of the loop-shaped tubing container.

23. The system of claim 19, wherein the loop reactor comprises a shell-and-tube configuration with a tube comprising the loop-shaped tubing container configured to receive the mono-olefin and the catalyst therein and a shell configured to receive heating and/or cooling medium.

* * * * *